US006953466B2

(12) United States Patent
Palasis et al.

(10) Patent No.: US 6,953,466 B2
(45) Date of Patent: Oct. 11, 2005

(54) METHODS FOR DELIVERING A THERAPEUTIC IMPLANT TO TISSUE

(75) Inventors: Maria Palasis, Wellesley, MA (US); James J. Barry, Marlborough, MA (US); Louis Ellis, St. Anthony, MN (US); Gary L. Hendrickson, Big Lake, MN (US); Kent D. Harrison, Maple Grove, MN (US); Lixiao Wang, Maple Grove, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

(21) Appl. No.: 10/837,612

(22) Filed: May 4, 2004

(65) Prior Publication Data

US 2004/0204672 A1 Oct. 14, 2004

Related U.S. Application Data

(60) Continuation of application No. 09/709,031, filed on Nov. 8, 2000, now Pat. No. 6,749,617, which is a continuation-in-part of application No. 09/516,531, filed on Mar. 1, 2000, now Pat. No. 6,238,406, which is a division of application No. 09/184,220, filed on Nov. 2, 1998, now Pat. No. 6,045,565.

(60) Provisional application No. 60/064,210, filed on Nov. 4, 1997.

(51) Int. Cl.[7] .............................................. A61B 17/32
(52) U.S. Cl. ..................................... 606/167; 606/181
(58) Field of Search ................................ 606/167, 171, 606/181, 184, 185, 159, 166, 41, 45, 52; 128/898

(56) References Cited

U.S. PATENT DOCUMENTS

| 4,760,131 A | 7/1988 | Sundsmo et al. ........... 530/356 |
| 4,790,311 A | 12/1988 | Ruiz ....................... 128/303.1 |
| 4,896,671 A | 1/1990 | Cunningham et al. ...... 128/642 |
| 5,047,026 A | 9/1991 | Rydell ........................ 606/48 |
| 5,093,877 A | 3/1992 | Aita et al. .................... 385/34 |
| 5,261,889 A | 11/1993 | Laine et al. ................ 604/164 |

(Continued)

FOREIGN PATENT DOCUMENTS

| DE | 296 09 350 U1 | 10/1996 |
| DE | 296 09 350 U 1 | 10/1996 |

(Continued)

OTHER PUBLICATIONS

International Search Report, PCT/US 01/42994.
European Search Report, Appln. No. EP 98 95 7545.

(Continued)

Primary Examiner—Kevin T. Truong
(74) Attorney, Agent, or Firm—Kenyon and Kenyon

(57) ABSTRACT

A method for delivering a therapeutic implant to a tissue is provided. This method includes providing an elongate catheter having a distal end including a lumen, providing a carrier including a therapeutic agent, placing the carrier including the therapeutic agent into the lumen, advancing the distal end of the catheter to the tissue, and depositing the carrier including the therapeutic agent into the tissue.

16 Claims, 11 Drawing Sheets

U.S. PATENT DOCUMENTS

| | | | |
|---|---|---|---|
| 5,287,861 A | 2/1994 | Wilk | 128/898 |
| 5,358,485 A | 10/1994 | Vance et al. | 604/22 |
| 5,364,393 A | 11/1994 | Auth et al. | 606/34 |
| 5,370,675 A | 12/1994 | Edwards et al. | 607/101 |
| 5,380,316 A | 1/1995 | Aita et al. | 606/7 |
| 5,389,096 A | 2/1995 | Aita et al. | 606/15 |
| 5,403,311 A | 4/1995 | Abele et al. | 606/49 |
| 5,405,376 A | 4/1995 | Mulier et al. | |
| 5,431,649 A | 7/1995 | Mulier et al. | 606/41 |
| 5,522,815 A | 6/1996 | Durgin, Jr. et al. | 606/50 |
| 5,551,427 A | 9/1996 | Altman | 128/642 |
| 5,569,462 A | 10/1996 | Martinson et al. | 424/424 |
| 5,591,159 A | 1/1997 | Taheri | 606/15 |
| 5,593,405 A | 1/1997 | Osypka | 606/15 |
| 5,607,405 A | 3/1997 | Decker et al. | 604/264 |
| 5,620,414 A | 4/1997 | Campbell, Jr. | 604/22 |
| 5,672,174 A | 9/1997 | Gough et al. | 606/41 |
| 5,681,308 A | 10/1997 | Edwards et al. | 606/41 |
| 5,683,366 A | 11/1997 | Eggers et al. | 604/114 |
| 5,697,882 A | 12/1997 | Eggers et al. | 604/114 |
| 5,700,259 A | 12/1997 | Negus et al. | 606/14 |
| 5,713,894 A | 2/1998 | Murphy-Chutorian et al. | 606/15 |
| 5,725,521 A | 3/1998 | Mueller | 606/7 |
| 5,725,523 A | 3/1998 | Mueller | 606/15 |
| 5,810,836 A | 9/1998 | Hussein et al. | 606/108 |
| 5,866,561 A | 2/1999 | Ungs | |
| 5,871,495 A | 2/1999 | Mueller | 606/185 |
| 5,988,059 A | 10/1999 | Ellis et al. | |
| 5,980,887 A | 11/1999 | Isner et al. | |
| 6,028,164 A | 2/2000 | Loomis | |
| 6,042,581 A | 3/2000 | Ryan et al. | 606/45 |
| 6,045,565 A | 4/2000 | Ellis et al. | |
| 6,053,911 A | 4/2000 | Ryan et al. | 606/33 |
| 6,053,924 A | 4/2000 | Hussein | 606/108 |
| 6,056,742 A | 5/2000 | Murphy-Chutorian et al. | 606/11 |
| 6,056,743 A | 5/2000 | Ellis et al. | 606/15 |
| 6,100,242 A | 8/2000 | Hammond et al. | |

FOREIGN PATENT DOCUMENTS

| | | |
|---|---|---|
| DE | 195 37 084 A 1 | 4/1997 |
| WO | WO 96/00112 | 1/1996 |
| WO | WO 96/35469 | 11/1996 |
| WO | WO 96/39830 | 12/1996 |
| WO | WO 96/39963 | 12/1996 |
| WO | WO 97/18768 | 5/1997 |
| WO | WO 97/29803 | 8/1997 |
| WO | WO 97/32551 | 9/1997 |
| WO | WO 97/44071 | 11/1997 |
| WO | WO 98/05307 | 2/1998 |
| WO | WO 98/16157 | 4/1998 |
| WO | WO 98/17186 | 4/1998 |
| WO | WO 98/44953 A | 10/1998 |
| WO | WO 99/29251 A | 6/1999 |
| WO | WO 00/15146 | 3/2000 |
| WO | WO 00/16704 | 3/2000 |
| WO | WO 01/08741 | 2/2001 |

OTHER PUBLICATIONS

Mirhoseini et al., Abstract entitled "Transventricular Revascularization by Laser", *Lasers in Surgery and Medicine*, 2(2), 1982, 1 page.

Gal et al., Abstract entitled "Analysis of Photoproducts Free Radicals and Particulate Debris Generated . . . ", *Lasers in Surgery and Medicine*, 11(2) 1991, 1 page.

Isner, J., Abstract entitled "Right Ventricular Myocardial Infarction", *JAMA*, v259, n5, Feb. 5, 1988, 12 pages.

Pickering et al., Abstract entitled "Proliferative Activity in Peripheral and Coronary Atherosclerotic Plaque . . . ", *J. Clin: Invest.*, ISSN 0021–9738, Apr. 1993, 1 page.

Vineberg et al., "Creation of Intramyocardial Pathways to Channel Oxygenated Blood Between Ventricular Arteriolar Zones", *Canad. Med. Ass. J.*, vol. 96, Feb. 4, 1967, 3 pages.

Vineberg, A., "Results of 14 Years' Experience in the Surgical Treatment of Human Coronary Artery Insufficiency", Canad. Med. Ass. J., vol. 92, Feb. 13, 1965, 8 pages.

Vineberg et al., "The Ivalon Sponge Procedure for Myocardial Revascularization", *Surgery*, vol. 47, No. 2, Feb. 1960, pp. 268–289.

Vineberg et al., "Treatment of Acute Myocardial Infarction by Endocardial Resection", *Surgery*, vol. 57, No. 6, Jun. 1965, pp. 832–835.

Walter et al., "Treatment of Acute Myocardial Infarction by Transmural Blood Suply from the Ventricualr Cavity", *European Surgical Research*, 3:130–138 (1971).

Khazei et al., "Myocardial Canalization", *The Annals of Thoracic Surgery*, vol. 6, No. 2, Aug. 1968, pp. 163–171.

Hershey et al., "Transmyocardial Puncture Revascularization", Geriatrics, Mar. 1969, pp. 101–108.

Press Release dated Oct. 21, 1996, "Doctor's Demonstrate Proof of Blood Flow Through Open TMR Channels Created with PLC Systems . . . ", 1 page.

Press/News Release dated Oct. 10, 1996, "Texas Fieart Institute Presents Study Comparing the Use of CO2 . . . ", 1 page.

Goldman et al., "Nonoperative Portacaval Shunt in Swine", *Investigative Radiology*, vol. 25, No. 5, May 1990, 5 pages.

Schumacher et al., "Induction of Neoangiogenesis in Ischemic Myocardium by Human Growth Factors", *Clinical Investigation and Reports*, Dec. 1, 1997, 6 pages.

Article entitled "Gene therapy improves leg circulation—next step heart?", 70th Scientific Sessions, published on or before Nov. 2, 1998, 2 pages.

Winslow, R., "Genetic Techniques Succeed in Treating Patients with Obstructed Blood Vessels", *The Wall Street Journal*, published on or before Nov. 2, 1998, 2 pages.

Kolata, G., "Gene Therapy Gives Blood a Path Around Leg Blockages, Researchers Say", *The New York Times*, Nov. 10, 1997, 2 pages.

Mack et al., "Cardiopulmonary Support and Physiology", *The Journal of Thoracic and Cardiovascular Surgery*, vol. 115, No. 1, Jan., 1998, 10 pages.

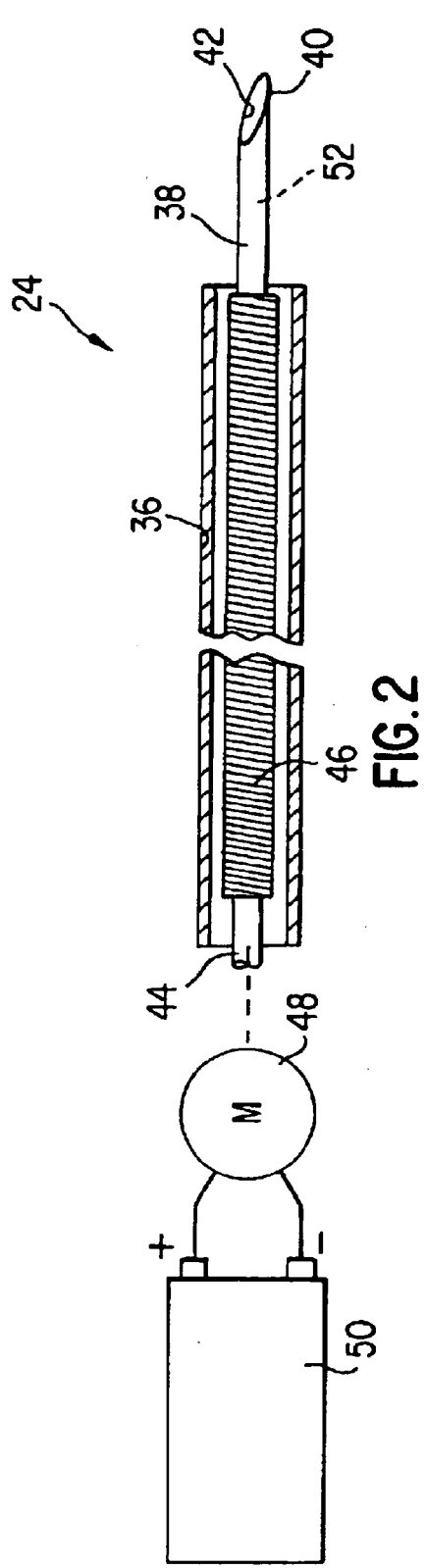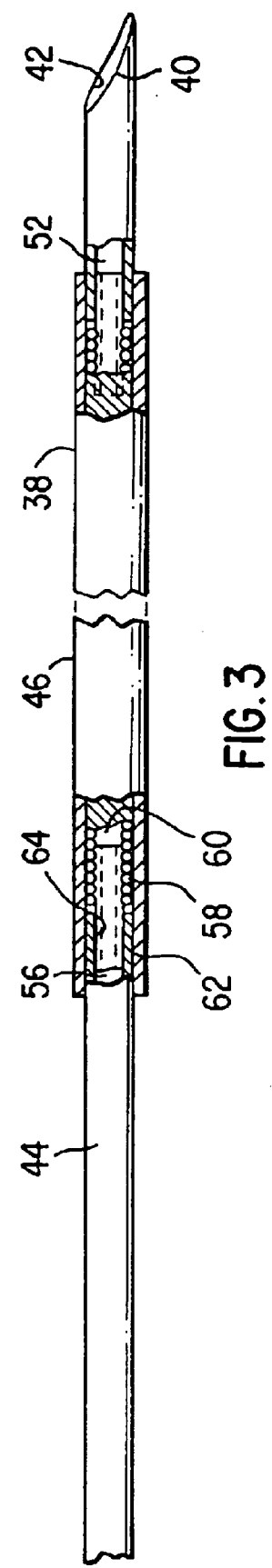

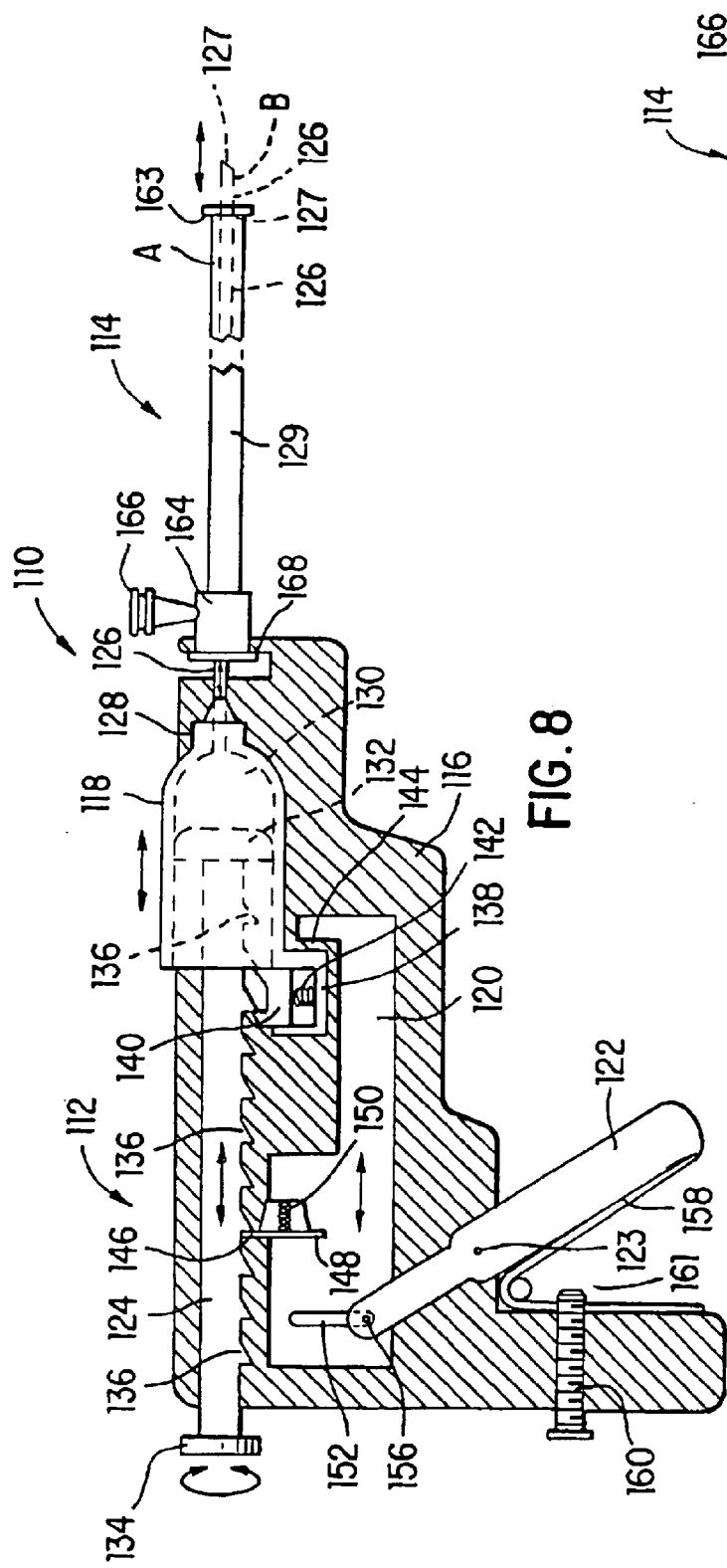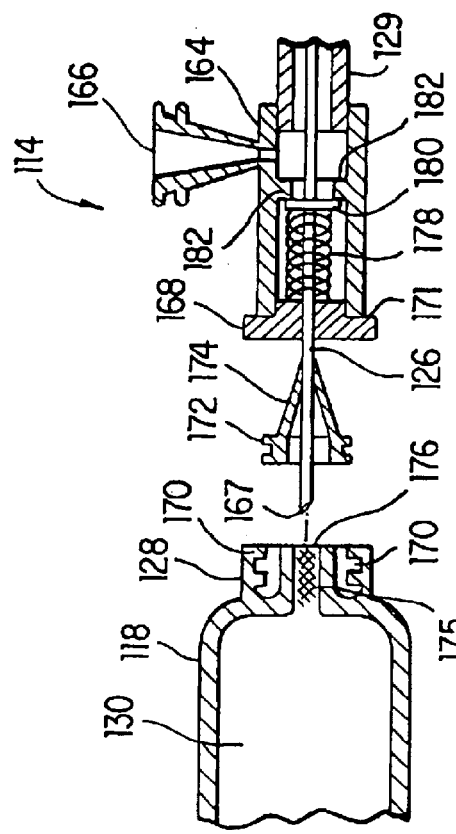

METHODS FOR DELIVERING A THERAPEUTIC IMPLANT TO TISSUE

CROSS REFERENCE TO RELATED APPLICATION

This application is a continuation of, and claims priority to, U.S. patent application Ser. No. 09/709,031, filed Nov. 8, 2000 now U.S. Pat. No. 6,749,617, entitled "CATHETER AND IMPLANTS FOR THE DELIVERY OF THERAPEUTIC AGENTS TO TISSUES," which is a continuation-in-part of, and claims priority to, U.S. patent application Ser. No. 09/516,531, filed Mar. 1, 2000 now U.S. Pat. No. 6,238,406, entitled "PERCUTANEOUS MYOCARDIAL REVASCULARIZATION GROWTH FACTOR MEDIUMS AND METHODS" which is a divisional of U.S. patent application Ser. No. 09/184,220 filed Nov. 2, 1998 now U.S. Pat. No. 6,045,565, which issued Apr. 4, 2000 and is entitled "PERCUTANEOUS MYOCARDIAL REVASCULARIZATION GROWTH FACTOR MEDIUMS AND METHODS" which claims the priority benefit of U.S. Provisional Patent Application Ser. No. 60/064,210, filed Nov. 4, 1997, entitled "TRANSMYOCARDIAL REVASCULARIZATION GROWTH FACTOR MEDIUMS AND METHOD" and U.S. Pat. No. 5,968,059, which issued Oct. 19, 1999, entitled "TRANS MYOCARDIAL REVASCULARIZATION CATHETER AND METHOD".

FIELD OF THE INVENTION

The present invention relates generally to the application of non-invasive techniques to the delivery of therapeutic agents. Specifically, the present invention relates to an injection catheter for the treatment of heart diseases or other organs by the injection of therapeutic agents and/or placement of implants.

BACKGROUND OF THE INVENTION

A number of techniques are available for treating heart disease and diseases of other organs percutaneously. An example of one such technique is percutaneous myocardial revascularization (PMR). This procedure is performed to increase blood perfusion through the myocardium of a patient. For example, in some patients, the number of lesions in coronary vessels is so great, or the location so remote in the patient vasculature, that restoring blood flow to the heart muscle is difficult. Percutaneous myocardial revascularization (PMR) has been developed as an alternative to techniques which are directed at by-passing or removing lesions. PMR is performed by boring holes directly into the myocardium of the heart. Positive results have been demonstrated in some human patients receiving PMR treatments. These results are believed to be caused in part by blood flowing from within a heart chamber through patent holes formed by PMR to the myocardial tissue. Suitable PMR holes have been proposed to be burned by laser, cut by mechanical means, and burned by radio frequency devices. Increased blood flow to the myocardium is also believed to be caused in part by the healing response to wound formation, specifically, the formation of new blood vessels in response to the newly created wound.

What remains to be provided are improvements and devices for enhancing the effectiveness of percutaneous myocardial revascularization. What also remains is the extension of these and other refinements to the treatment of various forms of heart disease and diseases of other organs.

SUMMARY OF THE INVENTION

The present invention includes devices and methods for treatment of heart disease and diseases of other organs. The primary focus of the devices and methods of the present invention is the treatment of heart disease, but it should be appreciated that, as explained in more detail below, the devices and methods can be used to treat the diseases of other organs. In some instances, the techniques will vary depending upon the disease being treated.

An exemplary embodiment of the present invention includes, devices and methods for increasing blood circulation to the myocardium. Circulation can be increased through patent holes into the myocardium from a heart chamber and from new blood vessel growth. New blood vessels can provide blood supplied from within a heart chamber, such as the left ventricle, and from pre-existing vessels in nearby healthy heart tissue. New vessel growth can be promoted by the healing response to wounds created in accordance with the present invention. New vessel growth can also be promoted by angiogenic substances supplied to the myocardium in accordance with the present invention.

One set of methods according to the present invention utilizes implants such as tubes implanted into the myocardium, preferably from within the heart, delivered by a catheter. The tubes preferably contain, or are coated with, an angiogenic substance capable of being released over time. These tubes can be biodegradable, being absorbed by the body, some embodiment tubes leaving a patent hole in the myocardium surrounded by the absorbed angiogenic material. Other PMR tubes are not biodegradable, but have lumens therethrough with side holes along the tube length, providing access to the myocardium from with the lumen. The non-biodegradable tube can be formed from a metal, polymer or other bio-stable material. The nonbiodegradable tubes are preferably coated with and contain releasable angiogenic material, promoting new vessel growth along the length of the tube, where the new vessels may be supplied with blood through the tube side holes. One method utilizes PMR tubes implanted into the myocardium from outside the heart and can be performed during open heart surgery or during a minimally invasive procedure. In one embodiment, a growth factor may be infused in a slow release polymer. The growth factor or drug and polymer can be placed in a tube having side poles for drug release. By placing the growth factor or drug in the polymer the growth factor or drug can be slowly released into the myocardium after implantation of the tube therein. In one embodiment of the tube containing the growth factor or drug and slow release polymer, the tube includes side holes and sealed ends.

Another set of methods according to the present invention involves injecting angiogenic material into the myocardium. A preferred method includes creating small bore holes or direct needle injection, for example using micro needles, into the myocardium utilizing a catheter within the heart. In the case of hole creation, a fluid, gel, polymer (biodegradable or biostable) or adhesive carrying an angiogenic material is injected into the hole. As the angiogenic substance is absorbed into the myocardium, in one method, a patent hole remains surrounded by myocardial tissue treated with angiogenic material. In another method, the injection hole closes, leaving no patent hole. New vessel growth is promoted by both the healing response to the wound and by the angiogenic substance. Blood circulation to myocardial tissue is increased by both the presence of the patent hole and the presence of new blood vessels supplied by existing coronary vessels and the heart interior. An alternative method utilizes angiogenic material injected into the myocardium from the exterior of the heart, in conjunction with open heart surgery or during a minimally invasive procedure.

In yet another alternate method, angiogenic materials delivered to the heart to promote new vessel growth. The new vessel growth is the consequence of the angiogenic material, for example, growth factor and any tissue reaction such as inflammation, rather than wounding the tissue.

Yet another set of methods includes externally wounding the heart and applying an external patch containing an angiogenic substance to the wound. The wound preferably penetrates into the myocardium. The healing response, enhanced by the angiogenic material, promotes new vessel growth near the wound. While the wound does not normally penetrate through to the heart chamber interior, new vessel formation can reach the chamber interior and also connect with pre-existing vessels in healthy heart muscle. A wound or series of wounds extending from healthy into hibernating tissue can create a network of vessels from healthy into hibernating tissue, supplying the hibernating tissue with blood. In another method, an external patch containing angiogenic material is applied to the heart without significant injury to the heart.

Any therapeutic agent, including small molecular drugs, proteins, genes and cells which could promote angiogenesis, protect tissues (i.e., cardiac protection), or promote tissue regeneration including Vascular Endothelial Growth Factor (VEGF) and Fibroblast Growth Factors (FGFs) is believed to be suitable for use with present invention. Carriers for the therapeutic agents of the present invention include polymers and angiopoietins including biodegradable and biostable hydrogels, and dissoluble polymers. Adhesives suitable for binding the present invention include fibrin glues and cyanoacrylates.

The injection of therapeutic agents and implantation of implants such as tubes for the placement of patches, is believed to have application to the treatment of other forms of heart disease in addition to the context of percutaneous myocardial revascularization. Some of these diseases include, for example, heart failure, myocardial infarction, and cancers, for example of the bladder, liver and kidneys.

BRIEF DESCRIPTION OF THE DRAWINGS

FIG. 2 is a partial cross-sectional schematic side view of a PNM catheter disposed within a guide tube;

FIG. 3 is a partial cross-sectional view of the PMR catheter of FIG. 2 in accordance with the present invention;

FIG. 8 is a cross sectional view of a catheter assembly in accordance with the present invention;

FIG. 9 is a cross sectional view of a detailed catheter assembly of FIG. 8;

DETAILED DESCRIPTION OF THE PREFERRED EMBODIMENTS

Figure 1:
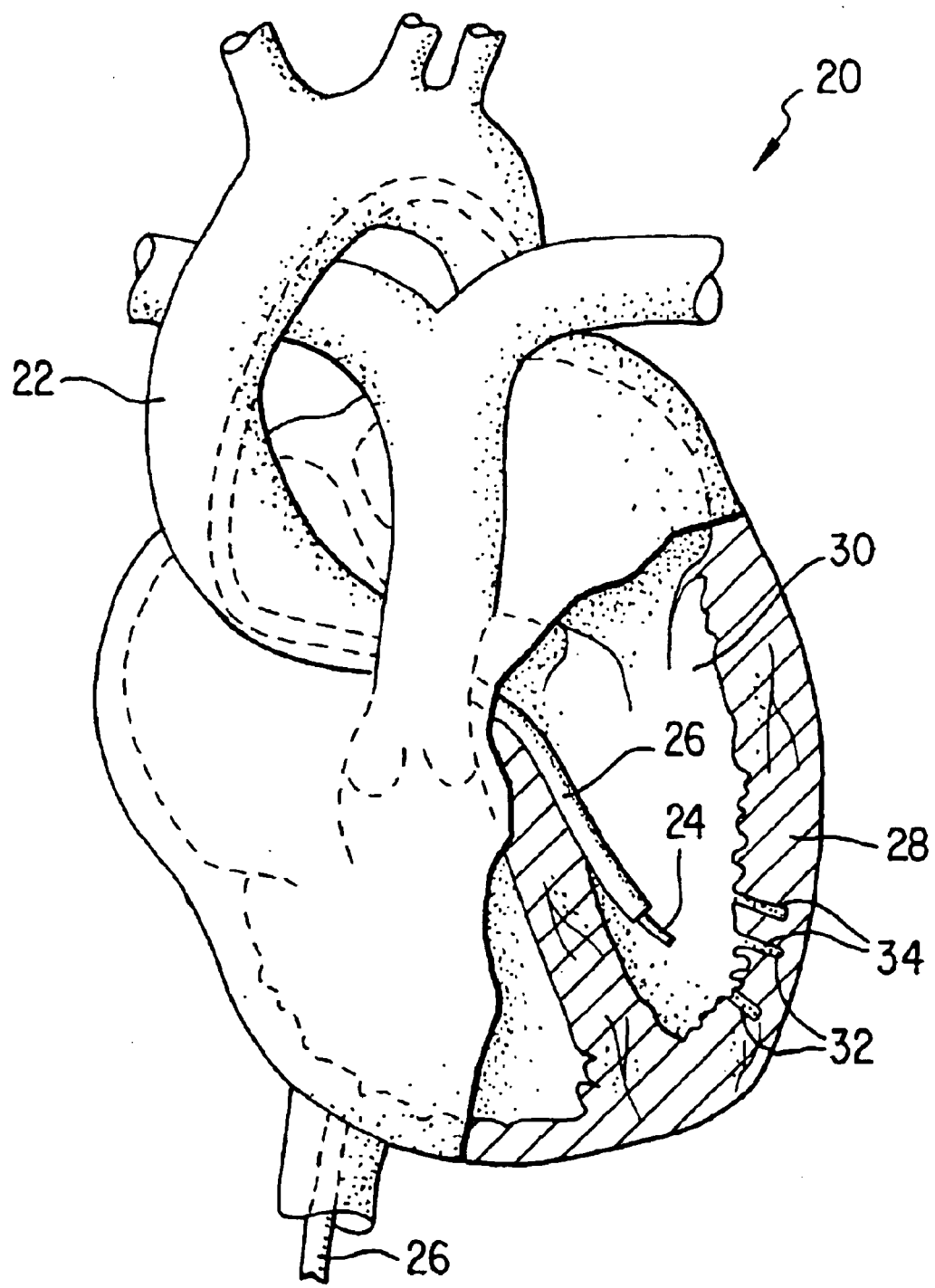
FIG. 1 is a perspective, cutaway view of a human heart having a PMR catheter inserted within, having punctured holes into the myocardium from within and filled the holes with angiogenic material.

Referring now to the drawings wherein like reference numerals indicate like elements throughout the several views, a human heart 20 having an aorta 22, a left ventricle 30, and a myocardium 28 is illustrated in FIG. 1. As shown for one embodiment of the invention, percutaneous catheter 24 is disposed within a guide catheter 26, which is disposed within aorta 22 and left ventricle 30. Catheter 24 has finished creating a series of holes or punctures 32 and filling them with a vascularization promoting, or angiogenic, substance 34 for the treatment of ischemic tissue. Angiogenic substance 34 is preferably carried in a biodegradable substance, such as, for example, gelatin, hyaluronic acid, albumin, and polyesters that are released over time. The carrier material can be adhered to secure the angiogenic substance in place and resist forces attempting to expel the materials into the heart chambers. The carrier need not, however, be biodegradable. The carrier material can include radiopaque material. The radiopaque material allows visualization of hole depth and expelled or washed out material.

After degradation of the biodegradable material, holes 32 can remain patent while the angiogenic material has promoted blood vessel growth near the hole walls and into the myocardium. Holes 32 can also close, leaving no patent hole but leaving newly formed blood vessels. The inventors believe the new vessel growth will be significantly enhanced by the angiogenic substance, thereby increasing blood flow from inside the left ventricle to the myocardium of the left ventricle. New vessel growth is expected to join with other vessels at anastomoses, forming a larger network of blood vessels in the myocardium supplied by blood from the left ventricle and blood from other vessels supplied by coronary arteries. Preferred substances for encouraging tissue growth of ischemic tissue include Vascular Endothelial Growth Factor (VEGF), Fibroblast Growth Factor (FGF), PDGF, angiopoietins (Ang1, Ang2), estrogen or genes effecting the production of growth factors such as MCP-1 and HIFI-α, DEL-1, Tat, and Akt.

Catheter 24 can be used to treat heart failure and the heart after myocardial infarction by directly injecting agents or implants into the diseased myocardium. Agents for treating heart failure include positive inotropic agents, diuretics, vasodilators, neurohormonal antagonists, calcium channel blockers, anti-ischemic agents, antiarrhythmics, anticoagulants; and natruiretic peptides, such as BNP, endothelian, growth hormone, and adenosine receptor antagonists. Survival genes or proteins may be used to treat heart tissue following myocardial infarction. These include, for example, AKT kinases, cyclases, i.e., adenylyl cyclase VI, IkB, or any anti-apoptotic molecule or protein, or other molecules which aid in heart muscle regeneration, such as the angiogenesis inducing agents listed above.

Catheter 24 can be used to treat cancers by injecting agents or implants into solid tumors or cancerous tissues, which are accessible endoluminally. Such agents for treatment of cancers include, for example, cytoxic proteins, such as FASL and TK/gancyclovir; or cytostatic agents, such as Rb or p53, or the genes encoding these proteins. Anti-angiogenic molecules can also be injected to treat cancer; these include, for example, endostatin, angiostatin, thrombospondin, dox-RGD, antibodies to or small molecule inhibitors of VEGF and other endogenous angiogenic molecules or other small molecules such as paclitaxel, 5-FU, etc.

Similarly to the substance for encouraging tissue growth used for the PMR treatment, the agents used to treat heart failure and the heart after myocardial infarction, as well as the agents used to treat cancer, can be incorporated into a carrier material. This material is preferably biodegradable or dissoluble but can be substantially bio-stable or non-biodegradable. The carrier material preferably holds the therapeutic agents in proximity to the tissue to be treated.

Such carriers can include, among others, biodegradable polymers suitable for use in the present invention include: poly(L-lactide) (PLLA), poly(D,L-lactide) (PLA), poly (glycolide) (PGA), poly(L-lactide-co-D.L. Lactide) (PLLA/PLA), poly(L-lactide-coglycolide) (PLA/PGA), poly (glocolide-co-trimethylene carbonate) (PGA/PTMC), polydioxanone (PDS), polycaprolactone(PCL), polyhydroxybutyrate (PHBT), poly(phosphazenes), poly(D,L-lactide-co-caprolactone) (PLA/PCL), poly(glycolide-cocaprolactone) (PGA/PCL), poly(phosphase ester) and polyanhydrides. Other materials suitable for mixing with growth factors include, for example: hydrogels, polyethylene oxide and its copolymers, polyvinylpyrolidone, polyacrylates, polyesters, gelatins, collagens, proteins, alginates, karaya gum, guar gum, agar, algin, carrageenans, pectins, xanthan, starch based gums, hydroxyalkyl and ethyl ethers of cellulose, sodium carboxymethyl cellulose, polyvinyl alcohol, and polyurethanes.

FIG. 2 is a partial cross sectional schematic side view of one embodiment of catheter 24 including an outer shaft 36 and inner shaft 38. Inner shaft 38 preferably includes a distally disposed cutting tip 40 having an opening 42 in fluid communication with a lumen 52 through tip 40. Inner shaft 38 preferably includes a proximal shaft portion 44 and a more flexible distal shaft portion 46. Inner shaft 38 is connected to a motor 48 for rotation of inner shaft 38 about the longitudinal axis thereof relative to outer shaft 36 which is fixed against rotation. Motor 48 is connected to a power supply shown schematically as a battery 50. The spacing between outer shaft 36 and inner shaft 38 should be enough to allow sufficient rotation of inner shaft 38 relative to outer shaft 36. Rotation is desirable as rotation acts to obliterate myocardial material within cutting tip 40, leaving a large diameter, patent hole. In one method, inner shaft 38 is not rotated relative to outer shaft 36, allowing injection of angiogenic material without leaving a large diameter myocardial hole. Inner shaft 38 is slidable longitudinally relative to outer shaft 36.

FIG. 3 is a side and partial cross sectional view of inner shaft 38 of PMR catheter 24 shown schematically in FIG. 2. Cutting tip 40 which is preferably a hypodermic needle tip having a distally disposed cutting edge 42 at an acute angle to the longitudinal axis of inner shaft 38. Tip 40 defines a lumen 52 in fluid communication with opening 42. Lumen 52 and opening 42 can be used to carry angiogenic materials and adhesives through tip 40, injecting it in a hole recently bored by tip 40. In some embodiments, radiopaque material is included with the angiogenic material. Radiopaque material or any contrast material used with guidance technology such as fluoroscopy, MRI or echocardiography allows confirmation of successful injection, visualization of hole depth, and visualization of any material expelled or washed from the hole. Although tip 40 is preferably formed from a hypodermic needle tip, it may be formed from other suitably durable and biocompatible materials as known to those skilled in the art. Tip 40 can have an outside diameter of, for example, 0.036 inches.

Proximal shaft 44 is preferably formed from a stainless steel hypotube which is more rigid than distal shaft 46. Shaft 44 defines a lumen 56 extending longitudinally therethrough. Proximal shaft 44 preferably extends the substantial majority of the length of inner shaft 38, to enhance the pushability and torqueability of inner shaft 38. It should be understood that although hypotube construction is preferred for proximal shaft 44, shaft 44 could be formed in the same manner as distal shaft 46 as described in more detail below or from another sufficiently torqueable and pushable construction as known in the art.

Distal shaft portion 46 is preferably more flexible than proximal shaft 44 to enhance trackability of inner shaft 38 proximate cutting tip 40. Distal shaft 46 can be formed from a helical coil 58 defining an elongate lumen 60 therethrough in fluid communication with lumen 56 of proximal shaft 44 and lumen 52 of cutting tip 40. Coil 58 can be surrounded by a polymer sheath 62. Sheath 62 may be PTFE, a shrink wrap or other similar biocompatible material known to those skilled in the art. The inside coil 58 forming the lumen wall of lumen 60 can be similarly coated. Shaft 46 can also be formed from an elastic alloy such as Nitinol.

Tip 40 and proximal shaft 44 can be connected to distal shaft 46 by two short tubular segments 64 and inserted within lumens 56 and 60, and 56 and 52, respectively. Tubular segments 64 can be small diameter hypotube segments or other sufficiently durable and biocompatible tubular members defining lumens in fluid communication with lumens 52, 56 and 60. An adhesive, braze or swage can be used to attach segments 64 to shafts 44 and 46 and tip 40.

In use, cutting tip 40 of inner shaft 38 can be delivered intravascularly to the heart wall and myocardium by a catheter tube or tubes. In one embodiment, once cutting tip 40 has been brought into contact with the heart wall, motor 48 can be activated to rotate cutting tip 40 and consequently blade 42. By further advancing cutting tip 40 into the myocardium of the heart, tissue in the path of the rotating blade will disintegrate. The disintegrated tissue can be aspirated through the lumen 52 extending through inner shaft 38. It can be appreciated that cutting tip 40 can penetrate the myocardium without being rotated. However, disintegration of tissue will generally not occur without rotating of tip 40.

Generally, the hole depth is preferably between $\frac{1}{3}$ and $\frac{3}{4}$ the thickness of the heart wall. The hole, however, could completely penetrate the myocardium for delivery of therapeutic agents to the pericardial space. The specific hole depth is determined on a case by case basis for each patient. Ultrasonic techniques may be used to view the patient's heart to determine the appropriate depth of the holes. In one method, radiopaque or contrast material is injected into the hole, in part to determine hole depth. A hole can be cut or formed, followed by radiopaque material injection and hole depth visualization using a method such as fluoroscopy. The cutting, radiopaque injection, and depth visualization cycle can be repeated until the desired hole depth is achieved. The depth of the holes will be generally proportional to the depth of penetration of cutting tip 40 into the myocardium. The rotation rate of cutting tip 40 may vary upon the character of the heart tissue encountered but should be rapid enough to disintegrate the tissue in the path of the cutting tip. The imaging agent can be incorporated into or mixed with a growth factor drug.

Inner shaft 38 and lumen 52 can be used to deliver angiogenic substances and adhesives and other carriers within the myocardium while tip 40 is still in place. In a preferred method, adhesives cure after leaving the tip. One method uses moisture cured adhesives. Once the angiogenic material has adhered to the walls of the hole bored into the myocardium, the angiogenic substance is more likely to remain in place within the myocardium. Adhesives preferably bind angiogenic material to the hole walls with a strength sufficient to resist immediate expulsion from the hole while being degradable or absorbable so as to allow diffusion of angiogenic material from the adhesive and absorption of angiogenic material into the myocardium. Inclusion of a fluoroscopic agent or radiopaque material with the angiogenic material can aid in visualizing expelled material.

Figure 4:
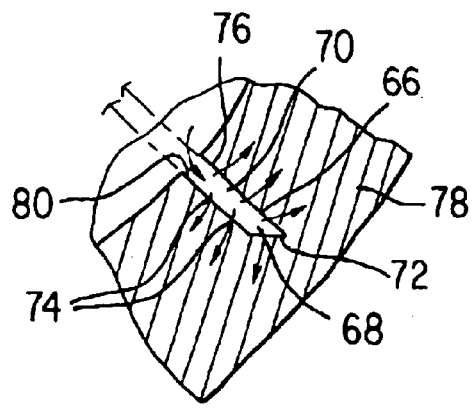
FIG. 4 is a side cross-sectional view of a PMR spike according to the present invention, having a lumen and side holes.

Referring now to FIG. 4, an implant, for example, tube 66 is illustrated implanted within a myocardial region 78. Tube 66 can be either biodegradable or permanent such as a non-biodegradable metal or polymer. PMR tubes are believed to operate by several mechanisms. First, driving the tubes into the myocardium is believed to trigger a healing response, including neovascularization. Second, the tubes can deliver angiogenic agents to the myocardium over a period of time. This can operate to promote new vessel growth in conjunction with, and apart from, the healing response. The delivery of growth factors can also speed the healing response generally, minimizing any adverse reaction to the implanted tube. Third, tubes having lumens and side holes can provide a hole within the tube for blood flow into the myocardium through the tube or a space for the therapeutic agent and slow release polymer.

A preferred embodiment tube has a circular cross section, a lumen 70, side holes 74, proximal port 80 and distal port 68, allowing blood flow through proximal port 80, lumen 70, side holes 74, distal port 68 and into myocardial tissue. Tube 66 is preferably formed of a biodegradable polymeric material, discussed further below. One embodiment has tubular walls porous to blood passage rather than larger, discrete holes. Another embodiment has no lumen and is formed of time-released therapeutics embedded in biodegradable material, such that the angiogenic substance is delivered within the myocardial tissue and the tube dissolves, possibly leaving a patent hole surrounded by tissue treated with angiogenic substance. While the preferred tube embodiment has a round cross-section, other embodiments have triangular, square, and elongate rectangular cross sections. Tube 66 preferably has a cutting tip 72 for easing insertion into the myocardium. Tubes can also have barbed outer surfaces to aid in retaining the spike within the myocardium. The tube can include radiopaque material or contrast as an aid in visualizing fluoroscopically where tubes have already been implanted. The tubes can be implanted in a pattern, leading from healthy tissue to hibernating tissue, creating a network of new blood vessels carrying both blood supplied from coronary arteries and the heart chamber itself The tube can be delivered through the lumen of a catheter from within a heart chamber. Tubes can also be delivered externally into the myocardium, either during open heart surgery or during a minimally invasive procedure. Tubes delivered externally preferably have lumens, side holes, closed proximal ends to minimize blood loss, and outside surface barbs to lessen the risk of the tube being expelled from the heart muscle. In a minimally invasive procedure, the PMR tubes can be injected through an elongate catheter into the pericardium. The PMR tubes can be injected entirely through the myocardium or can stop short of such penetration. The inventors believe the externally inserted PMR tubes can significantly promote vascularization within the myocardium, even where the PMR tubes do not penetrate through to the endocardium.

Although tubes 66 have been described herein with respect to PMR, it is anticipated that the tubes can be used for the treatment of heart failure and the heart after myocardial infarction by incorporating the therapeutic agents described above with respect to these conditions. It is also believed that the tubes could be used for treating cancer by incorporating the therapeutic agents described above.

Figure 5:
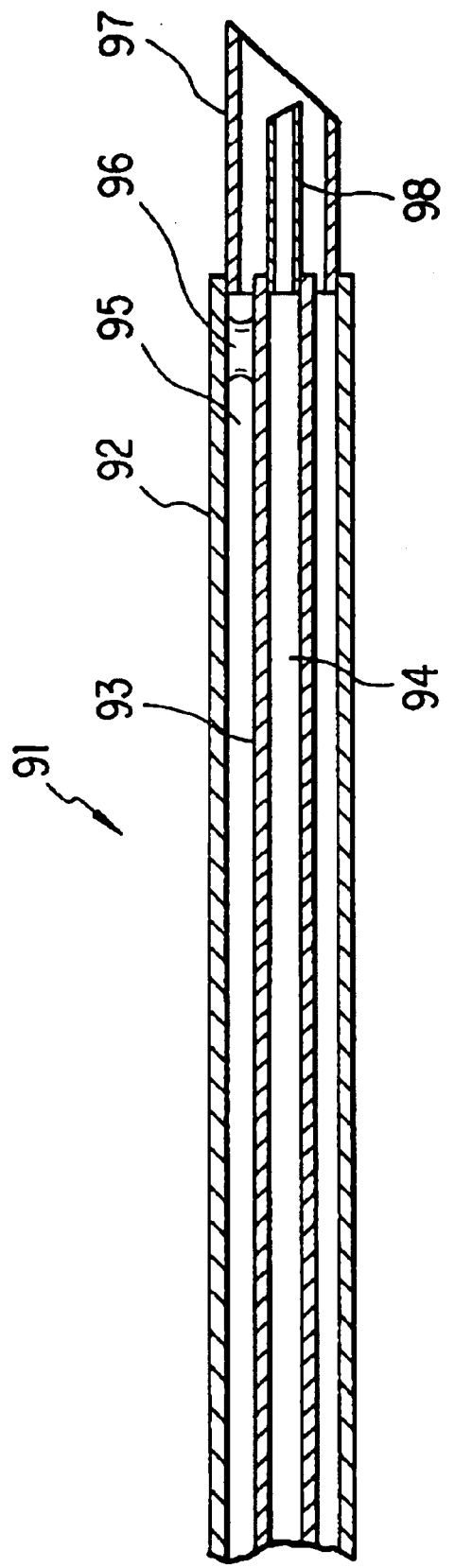
FIG. 5 is a cross-sectional view of a catheter assembly in accordance with the present invention, for placement of an in situ implant.

FIG. 5 is a cross-sectional view of a catheter 91 for placement of an in situ implant including a therapeutic agent. Catheter 91 includes an elongate outer tube 92 and an elongate inner tube 93 having a lumen 94 extending therethrough. An annular lumen 95 defined between tubes 92 and 93. At the proximal end of tubes 92 and 93 (not shown) is a suitable manifold, as known to those skilled in the art, including a first infusion port in fluid communication with lumen 94 and a second infusion port in fluid communication with lumen 95. The ports should be separately connected to the respective lumens 94 and 95 such that fluids infused through each port are not co-mingled in the lumens. In addition to the proximal manifold holding the relative positions of tubes 92 and 93, a web or adhesive weld 96 disposed at the distal end of tubes 92 and 93 can substantially fix the tubes relative position. Extending distally from tube 92 is a sharpened tube, which could be a hypotube 97. Extending from tube 93 and through the lumen of tube 97 is a sharpened tube 98 having a lumen extending therethrough. The lumen of tube 98 is in fluid communication with lumen 94 and the lumen through tube 97 is in fluid communication with lumen 95.

Tubes 92 and 93 should be long enough and flexible enough to be advanced intra-luminally to a desired body organ such as the heart, liver, bladder, or kidneys. The diameter of tube 92 should be sufficiently small to be advanced through the desired body lumen. Tubes 92 and 93 can be formed from biocompatible polymers or other materials known to those skilled in the art. Tubes 97 and 98 can be adhered to tubes 92 and 93 respectively by materials known to those skilled in the art. Tubes 97 and 98 can be hypotubes made from a metallic material or from a sufficiently rigid polymer or other material that they can be advanced into tissue for fluid injection therein.

As an alternative to the tubular implants described above, catheter 91 can be used to form an in situ implant. For example, a polymer could be pre-mixed with any of the therapeutic agents described above for treatment of the heart, liver, kidneys, bladder or other organs and solid tumors. The polymer pre-mix could be infused through, for example, lumen 94 into a tissue to be treated. At the same location a cross-linking agent could be infused through lumen 95 into the tissue. This would result in the polymer becoming cross-linked and solidifying in tissue. The cross-linking agent can also be mixed into a contrast solution such that the implants would become radiopaque. An example polymer to be pre-mixed with the therapeutic agent is alginate polymer, which can be cross-linked by multivalent ions. In another example, the polymer, if a polycation, gelatin, chitosan or the like which can be delivered through one lumen and the therapeutic agent if a polyanion such as DNA can be delivered through the second lumen. A polyelectrolyte complex will be formed when the polycation mixes with the polyanion, forming a solid material.

The polymer can be bio-stable or biodegradable, including dissoluble polymers. After the implants are placed in the tissue, the therapeutic agent is slowly released. The rate of release of the therapeutic agent to the surrounding tissue may be controlled by, for example, 1) diffusion of the agent through the polymer implant if the polymer implant is bio-stable; 2) by the rate of polymer degradation or dissolution if the implant is made of a biodegradable or dissolvable implant; or 3) by the rate of ion exchange if the implant is formed using two oppositely changed polyelectrolytes. In this manner, therapeutic agents may be delivered to tissue over periods of days, weeks, or a longer period of time.

An alternate embodiment of an implant which can be injected through a single lumen catheter such as that shown in FIG. 3 includes genetically engineered cells (such that they over express specific therapeutic proteins) grown in scaffolding polymers, that can be implanted into tissue. The implants may contain specific cells which have therapeutic properties in certain instances such as endothelial cells. In an alternate embodiment, the implants may also be healthy tissue taken from one site and transplanted to a diseased site using, for example, a needle injection catheter such as that shown in FIG. 3.

Figure 6:
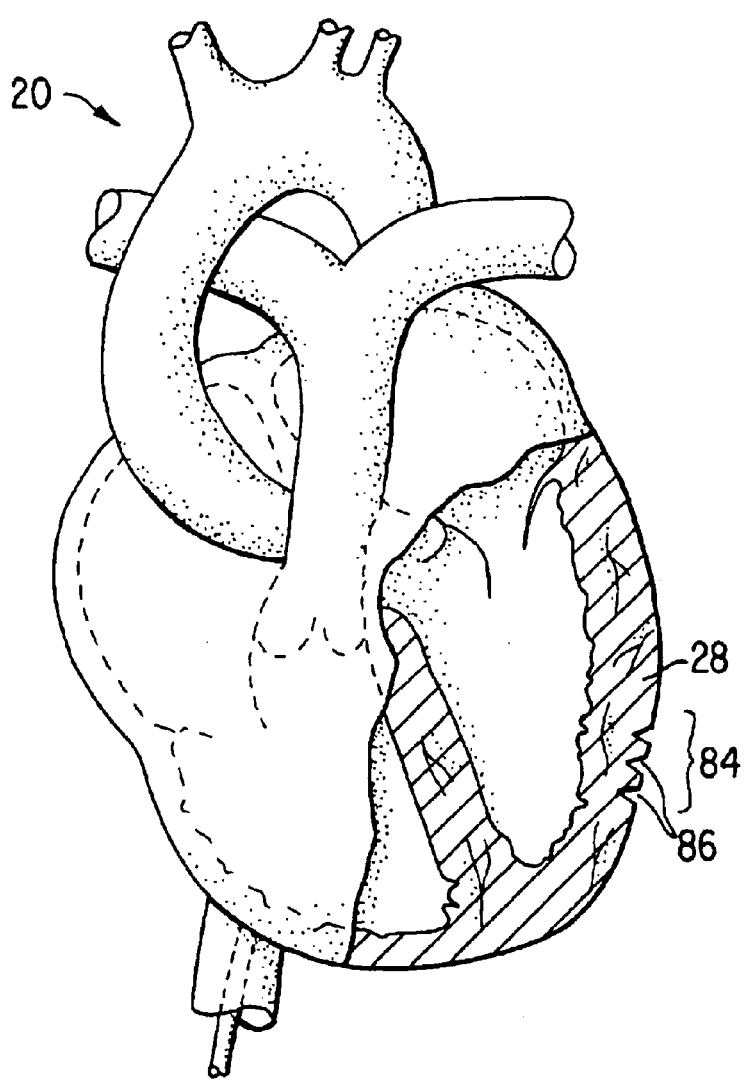
FIG. 6 is a perspective, cut-away view of a human heart having an external wound to the wall of the left ventricle.
Figure 7:
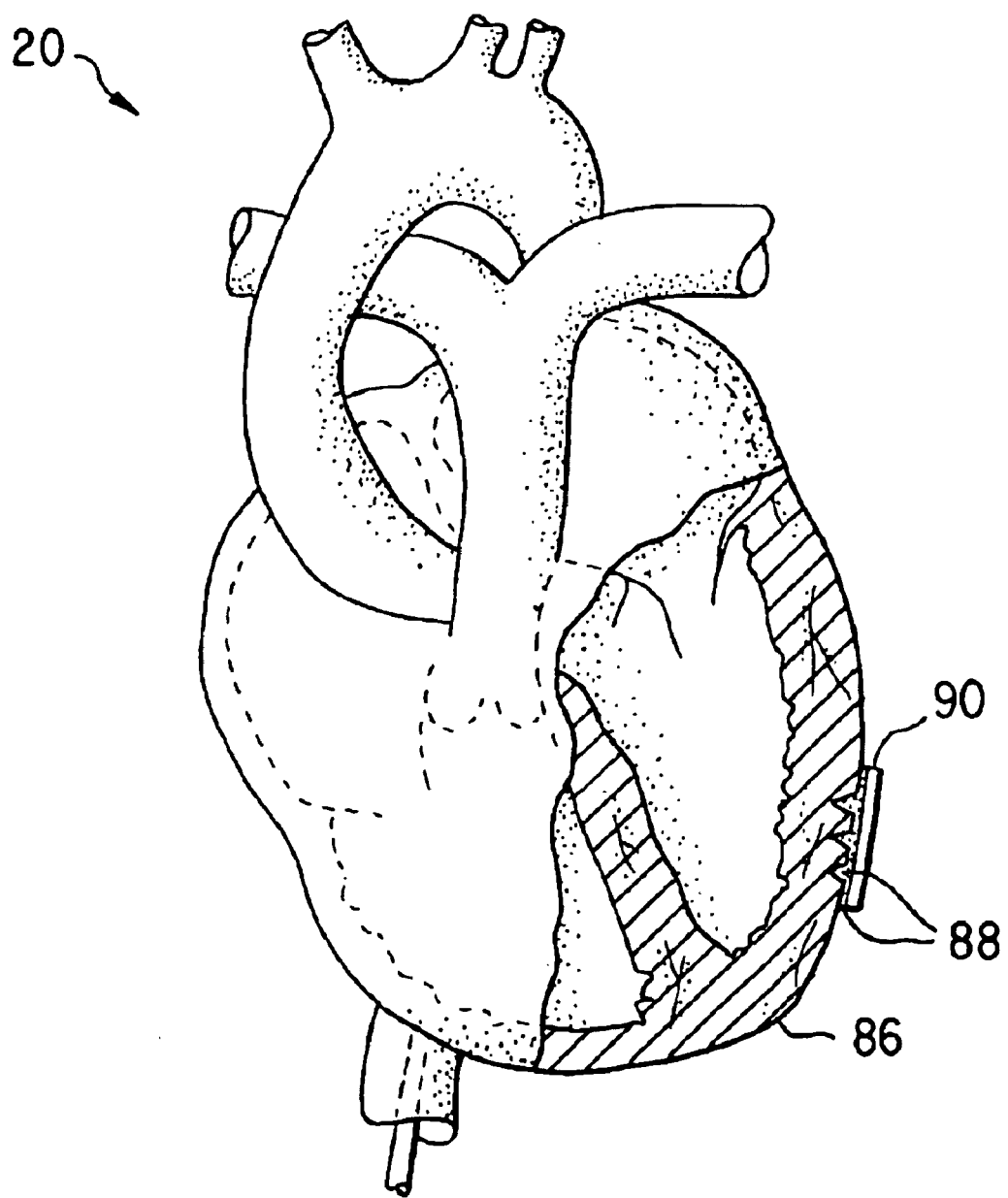
FIG. 7 is a perspective, cut-away view of the wounded heart of FIG. 6 having angiogenic substance and patch applied.

Referring now to FIG. 6, another procedure for promoting vascularization within the myocardium is illustrated. Heart 20 has a wound 84 external to the left ventricle. Wound 84 is formed of a series of incisions 86 through the pericardium into the myocardium. In one method, the wounds are formed as a series of needle punctures rather than wedge like incisions as illustrated in FIG. 6. Referring now to FIG. 7, after wound formation, angiogenic substances, wound healing agents, and growth factors can be applied to the wound, promoting a healing response. Growth factors and healing agents may be included to promote healing of the wounds to the heart, desirable even apart from the angiogenic goal. A patch 90 can then be applied over the wound, holding the angiogenic substance in place over the wound. In one embodiment, the patch is held in place with adhesives.

Patch 90 is preferably biodegradable, capable of being absorbed by the body after it is no longer needed. One patch includes a reservoir of angiogenic substance that leaches out the inside of the patch, supplying more wound healing and angiogenic compound over time.

Externally wounding the heart and applying a patch can be performed in conjunction with open heart surgery, where the heart is available for such a procedure. Minimally invasive procedures can also be used to access the heart for externally wounding the heart, creating wound and applying patch through a relatively small opening. Applicants believe externally wounding the heart triggers a healing response within the myocardium, including the formation of new blood vessels to the wounded area. While the incisions preferably do not penetrate through the entire thickness of the chamber wall, applicants believe the incisions within the myocardium trigger new blood vessel growth within the myocardium which can be supplied by vessels within the heart chamber or by other coronary vessels. While it is believed to be preferable to wound the tissue prior to placement of the patch, the patch is believed to have therapeutic value as well when placed on tissue that has not been wounded.

A variety of angiogenic substances and growth factors can be used in accordance with the present invention. Growth factors such as Fibroblast Growth Factor (FGF, FGF1, FGF-2), Vascular Endothelial Growth Factors (VEGF) (all constructs including VEGF-2) and Endothelial Mitogenic Growth Factors are among the growth factors preferred for use with the present invention. Angiogenic substances such as estrogen, including estradiol(E2), estriol(E3) and 17-Beta Estradiol are also believed suitable for use with the present invention. Estrogen is believed to induce angiogenesis and increase permeability. This provides increased local blood circulation through neovascularization. Gene transfer into the heart tissue can be done as well.

The therapeutic agents used in the present invention also include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA, DNA, cDNA or RNA in a noninfectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22"), and viral liposomes and cationic polymers that are selected from a number of types depending on the desired application. For example, biologically active solutes include anti-thrombogenic agents such as heparin, heparin derivatives, urokinase, PPACK (dextrophenylalanine proline arginine chloromethylketone), rapamycin, probucol, and verapamil; angiogenic and anti-angiogenic agents; antiproliferative agents such as enoxaprin, angiopeptin, or monoclonal antibodies capable of blocking smooth muscle cell proliferation, hirudin, and acetylsalicylic acid; antiinflammatory agents such as dexamethasone, prednisolone, corticosterone, budesonide, estrogen, sulfasalazine, and mesalamine; antineoplastic/antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl ketone, an RGD peptide-containing compounds, heparin, antithrombin compounds, platelet receptor antagonists, anti-thrombin antibodies, anti-platelet receptor antibodies, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifuctional molecules consisting of an antibody and a cytotoxin; cholesterol-lowering agents; vasodilating agents; agents which interfere with endogenous vasoactive mechanisms, and combinations thereof Cells of human origin can be used (autologous or allogeneic) or from an animal source (xenogeneic), genetically engineered if desired to deliver proteins of interest at the transplant site. The delivery media can be formulated as needed to maintain cell function and viability.

Polynucleotide sequences useful in the practice of the present invention include DNA or RNA sequences having a therapeutic effect after being taken up by a cell. Examples of therapeutic polynucleotides include anti-sense DNA and RNA; DNA coding for an antisense RNA; or DNA coding for tRNA or rRNA to replace defective or deficient endogenous molecules. The polynucleotides of the invention can also code for therapeutic peptides. A polypeptide is understood to be any translation product of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body. In addition, the polypeptides or proteins that can used include without limitation, angiogenic factors including acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor; growth factors; cell cycle inhibitors including CDK inhibitors; thymidine kinase ("TK") and other agents useful for interfering with cell proliferation, including agents for treating malignancies; and combinations thereof Still other useful factors, which can be provided as polypeptides or as DNA encoding these polypeptides, include monocyte chemoattractant protein ("MCP-1"), and the family of bone morphogenic proteins ("BWPs"). The known proteins include BMP-2, BMP-3, BMP-4, BMP-5, BMP-6 (Vgr1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a DMP can be provided. Such molecules include any of the "hedgehog" proteins, or the DNAs encoding them.

In one exemplary embodiment of the present invention, the medical device has recombinant nucleic acid incorporated therein, wherein the recombinant nucleic acid comprises a viral vector having linked thereto an exogenous nucleic acid sequence. "Exogenous nucleic acid sequence" is used herein to mean a sequence of nucleic acids that is exogenous to the virus from which the vector is derived. The concentration of the viral vector, preferably an adenoviral vector, is at least about $10^{10}$ plaque forming units ("p.f.u."), preferably at least about $10^{11}$ p.f.u. Alternatively, the concentration of the viral vector is limited by the concentration that results in an undesirable immune response from a patient.

A variety of adhesives are suitable for the present invention, both for adhering a patch over a heart wound, and for retaining angiogenic material within a wound. Biodegradable polymer and materials are suitable for mixing with the therapeutic agents as described with respect to the other embodiments above. One adhesive is a hydrogel composed of gelatin and poly(L-glutamic acid)(PLGA). The hydrogel is formed by chemically cross linking gelatin and poly(L-glutamic acid). Another adhesive is fibrin glue. One suitable fibrin glue includes fibrinogen, thrombin, calcium chloride and factor VIII. Another family of adhesives is cyanoacrylates. Preferred cyanoacrylates include butyl-2-cyanoacrylate (Histoacryl), ethyl-2-cyanoacrylate, and octyl-2-cyanoacrylate. Gelatin-resorcinol formaldehyde-glutaraldehyde is another suitable adhesive.

Applicants believe many polymers having suitable adhesive properties can also be utilized, including without limitation: polyurethanes having amino groups, di- and trifunctional diols; polyvinyl acetates; polyamides; polyvinyl alcohols; polystyrenes; polylactides; polylactones; block co-polymers including polyesters, polyamides, and polyurethanes; and combinations and mixtures thereof Growth factors, angiogenic substances and biodegradable carriers and adhesives can be applied internally to punctures within heart chamber walls, externally to external heart wounds, and incorporated into tubes or spikes for implantation into the myocardium or other organs or solid tumors.

It is anticipated that the patch of the present invention can be used to treat heart failure, heart tissue following myocardial infarction and cancers, in addition to ischemic tissue. In each instance, the therapeutic agents described above with respect to those conditions could be incorporated into the patch for delivery to the tissue. In the case of heart failure, the treatment of heart tissue following myocardial infarction and the treatment of cancer, it is believed that the patch would be placed directly on, or in close proximity to the tissue to be treated.

FIG. 8 is a schematic view of an alternate catheter assembly 110 including a dosage actuator gun 112 and catheter 114. Catheter assembly 110 can be used to inject the growth factors, angiogenic materials and other substances in accordance with the present invention. Catheter 24 can be used for percutaneous myocardial revascularization (PMR) of ischemic heart tissue delivery of agents to the myocardium of a patient suffering from congestive heart failure, delivery of agents to salvage injured myocardium following myocardial infarction, and to inhibit growth of cancerous tissues by delivering agents to organs such as the bladder, liver or kidneys.

Gun 112 includes a body 116. Slidably disposed within body 116 and schematically shown in FIG. 7 is a syringe 118, slider body 120 and plunger 124. Syringe 118, slider body 120 and plunger 124 are slidable proximally and distally as shown by the arrows adjacent these respective elements. Trigger 122 is pivotally connected about pin 123 to body 116. It can be appreciated that those skilled in the art of mechanical design could readily fashion a gun 112 based on the schematic description herein.

Catheter 114 includes an inner tubular shaft 126. Inner tubular shaft 126 includes a sharpened distal end 127. Like syringe 118, slider 120 and plunger 124, inner shaft 126 can be moved proximally or distally as shown by the arrows. More particularly, inner shaft 126 can be moved from a proximal position A wherein tip 127 is disposed within an outer shaft 129 of catheter 114 to a second position B, wherein tip 127 is disposed distally of outer shaft 129.

Syringe 118 includes an inner chamber 130 for containing a dosage of a drug or other fluid. Disposed at the distal end of plunger 124 is a plunger seal 132. Syringe 118 including plunger seal 132 preferably are prepacked to contain a quantity of drug, agent or other fluid prior to placement in gun 112. Syringe 118 includes a Luer fitting 128 or similar attachment device to fluidly connect inner shaft 126 to syringe 118. The proximal ends of plunger 124 includes a handle 134. Handle 134 can be used to rotate plunger 124 about its longitudinal axis within housing 116. Plunger 124 includes a plurality of teeth 136 extending therefrom. Syringe 118 also includes a cradle 138 in which is disposed a one-way plunger lock 140 which is biased toward plunger 124 by spring 142. Lock 140 includes one or more teeth having a slope which allows teeth 136 of plunger 124 to be advanced distally thereover, but engages with teeth 136 to prevent plunger 124 from being withdrawn proximally. Plunger 124 can, however, be withdrawn proximally if it is rotated about its longitudinal axis by using handle 134 such that teeth 136 are disposed away from lock 140, for example, pointed upward rather than downward as shown in FIG. 8.

Slider 120 includes a syringe restraint member 144 which includes a surface engageable with cradle 138 of syringe 118. A plunger advancing member 146 is pivotally attached to slider 120 by pin 148. A spring 150 biases advancing member 146 toward a vertical position as shown in FIG. 8. As slider 120 moves proximally relative to plunger 124, advancing member 148 pivots downwardly as shown by the arrow allowing slider 120 to move proximally relative to plunger 124. Advancing member 146, however, will pivot back to the vertical position after passing over a tooth 136 and be braced in the vertical position by slider 120 to engage the vertical proximal side of one of the teeth 136. Slider 120 includes a slot 152. A pin 156 extends through an end of trigger 122 and is slidable within slot 152. A spring 158 biases trigger 122 into the position shown. Trigger 122 is, however, pivotable in the direction shown by the arrow about pin 123 between the position shown and an adjustment screw 160. Adjustment screw 160 has a distal end 161 which is engageable with trigger 122 to limit the pivoting of trigger 122 in a clockwise direction about pin 123.

Catheter 114 includes a preferably radiopaque, atraumatic hood 163 at its distal end and a manifold 164 at its proximal end. Manifold 164 includes a port 166 for infusion or withdrawal of fluids from catheter 114 through a lumen defined between inner shaft 126 and outer shaft 129. Manifold 164 also includes a flange 168 engageable with a portion of body 116 to connect body 116 to catheter 114.

FIG. 9 is a cross sectional view of a portion of the catheter assembly 110 including a portion of catheter 114 including syringe 118. Luer fitting 128 includes a threaded portion 170 engageable with a threaded portion 172 of a compatible Luer fitting 174 connected to inner shaft 126. Syringe 118 defines an inner shaft receiving lumen 175 sealed with polymer or rubber seal 176 which can be punctured by a sharpened distal end 167 of inner shaft 126 when threads 162 are advanced into threads 170. A fluid connection thus results between the lumen through inner shaft 126 and chamber 130. Flange 168 can be part of a seal 171 which creates a substantially fluid-tight seal between inner shaft 126 and manifold 164 while allowing inner shaft 126 to move proximally and distally in the direction as shown by the arrow within manifold 164 of outer shaft 129. A spring 178 biases inner shaft 126 distally relative to manifold 164 and outer shaft 129. The travel of inner shaft 126 distally is limited by engagement of a stop disc 180 with stop ring 182 of manifold 164.

Figure 10:
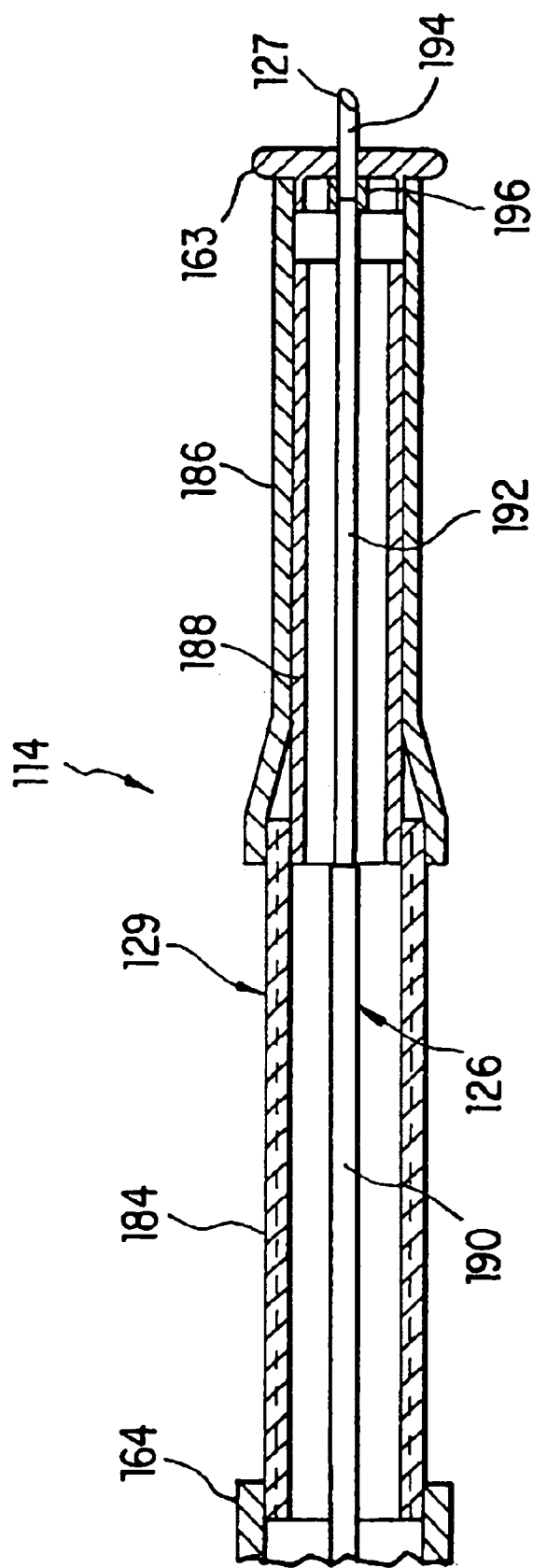
FIG. 10 is a cross sectional view of a catheter portion of the catheter assembly of FIG. 7.

FIG. 10 is a cross sectional view of a preferred embodiment of catheter 114 including inner shaft 126 and outer shaft 129. As shown in FIG. 10, outer shaft 129 is connected by suitable heat adhesive to manifold 164. Outer shaft 129 includes a proximal portion 184 which is preferably a co-braided member having, for example, an inner and outer layer of PEBA and a stainless steel reinforcing braid disposed therebetween. Outer shaft 129 also preferably includes a distal portion including a spring coil 188 and an outer polyethylene sheath 186. Connected to the distal end of sheath 186 is hood 163. Hood 163 is preferably formed from an atraumatic material and can include radiopaque material to enhance visibility by fluoroscopy. Inner tube 126 preferably includes a proximal portion 190 which can be formed from, for example, heat treated stainless steel and a distal portion 192 which is preferably formed from a Nitinol hypotube. A needle 194 having a distal tip 127 is preferably attached to the distal end of distal tube 192 by a swage collar 196, which may be radiopaque, can engage with hood 163 to limit the distal travel of inner shaft 126 relative to outer shaft 129.

It can be appreciated by those skilled in the art that there are numerous materials which can be advantageously used to construct the apparatus disclosed herein. These materials should be selected in view of the use to which the apparatus is put.

In use, catheter 114 can be advanced into a chamber of the heart, for example, the left ventricle through a femoral, brachial or carotid artery approach similar to catheter 24 of FIG. 1. Hood 163 of catheter 114 is brought into contact with the endocardium of the chamber at a selected location. Chamber 130 of syringe 118 is preferably preloaded with a drug or growth factor of the type, for example, as described previously. Trigger 122 is then pivoted in a clockwise direction from the position shown in FIG. 8 toward set screw 160. This will cause slider 122 to slide in a distal direction. When trigger 122 is in the position shown in FIG. 8, tip 127 of inner shaft 126 will be in position A, withdrawn into outer shaft 129. As slider 120 is slid distally, however, restraint member 144 will also advance distally allowing syringe 118, inner shaft 126 and tip 127 to advance distally under the influence of spring 178 such that distal tip 127 will be disposed in position B distally of hood 163. When tip 127 is in position B, stop plate 180 will engage stop ring 182 as shown in FIG. 8. When tip 127 is in position A, however, plate 180 will be spaced proximally from ring 182.

Substantially simultaneously with the advancement of tip 127 from position A to position B, plunger advancing member 146 will engage the proximal side of one of the teeth 136 and advance plunger 136 distally into reservoir 130 to advance a dosage of drug or growth factor through inner shaft 126 and out tip 127 which, in position B would be disposed within the myocardium. The amount of the dosage can be regulated by limiting the travel of trigger 122 by adjusting screw 160. It can be appreciated that ring 182 should limit the travel in the distal direction of inner shaft 126 and syringe 118 to a distance less than the distal travel of plunger 124 such that there can be relative advancement of plunger 124 into chamber 130 to advance drug or growth factor through inner shaft 126.

When trigger 122 is released, it will pivot in a counter-clockwise direction back to the position shown in FIG. 8 under the influence of spring 158. As trigger 122 pivots in a counterclockwise direction back to its original position, plunger 124, and advancing member 146 pivots in a clockwise direction to slide over the slopped proximal end of one or more teeth 136. Syringe 118 and inner shaft 126 are slid proximally by the engagement of member 144 with cradle 138. Once trigger 122 has attained its original position, the trigger can be pulled again to advance tip 127 and deliver another dosage of drug or growth factor to the myocardium.

Figure 11:
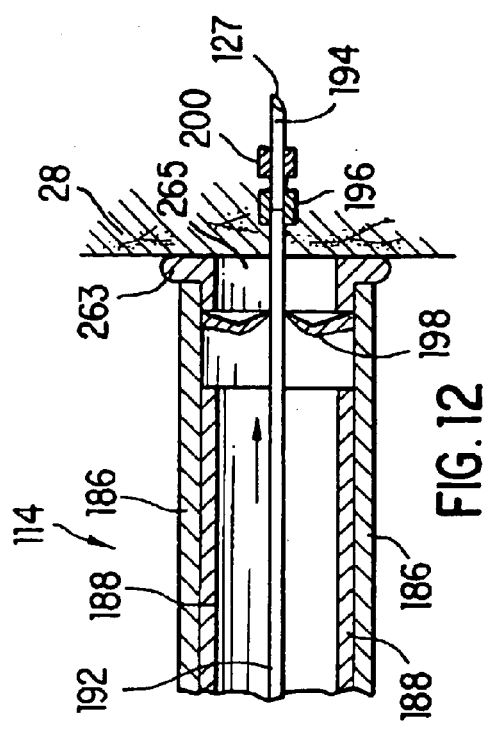
FIG. 11 is a cross sectional view of a catheter tip showing a radiopaque marker disposed within the catheter.

FIG. 11 is a side view of an alternate distal portion of a catheter 114. In this embodiment, catheter 114 includes a hood 263, which like hood 163 is preferably made from atraumatic material and can include radiopaque material to enhance visibility by fluoroscopy. Hood 263, however, includes a larger diameter opening 265. Disposed just proximal hood 263 is a annular shaped brush 198 which is in contact with and surrounds needle 194. Disposed loosely on needle 194 is a radiopaque marker band 200 which can be formed from a suitable metal or bio-stable or biodegradable material loaded with a radiopaque agent. Hood 263, as shown in FIG. 11, is disposed against the endocardium proximate myocardium 28.

Figure 12:
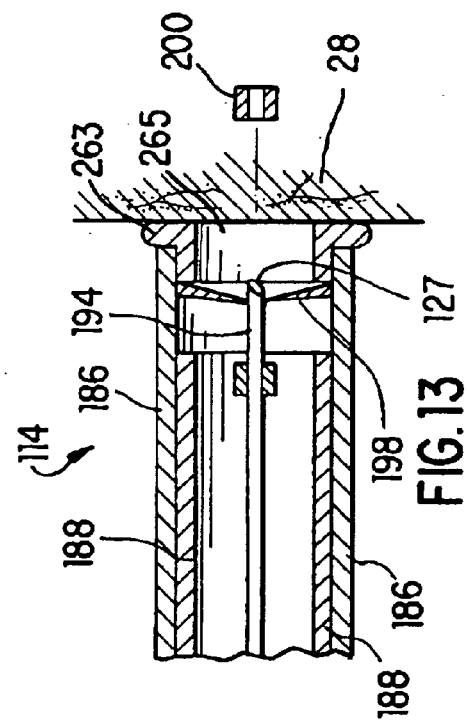
FIG. 12 is a view of the catheter tip of FIG. 11 showing the radiopaque marker distal of the catheter tip.
Figure 13:
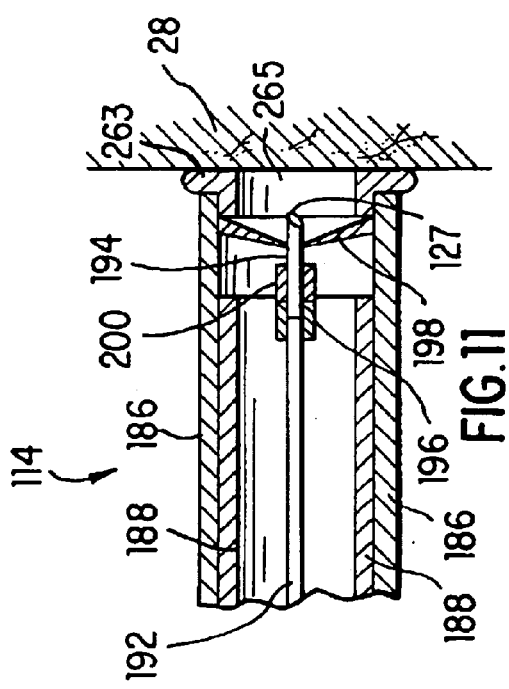
FIG. 13 is a view of the catheter tip of FIG. 11 showing the radiopaque marker disposed within the myocardium.

In FIG. 12, needle 194 has been advanced distally beyond the distal end of hood 263 such that radiopaque marker 200 is disposed within myocardium 128. In FIG. 13, needle 194 has been withdrawn proximally into catheter 114 while marker 200 remains behind in myocardium 28.

Marker 200 can be used for mapping purposes, for example, to define a target zone or perimeter for subsequent PMR treatment. Marker 200 can also be used chronically for future PMR treatments, diagnosis and monitoring. Marker 200 can also be coated or impregnated with a growth factor, drug or other therapeutic agent.

Figure 14:
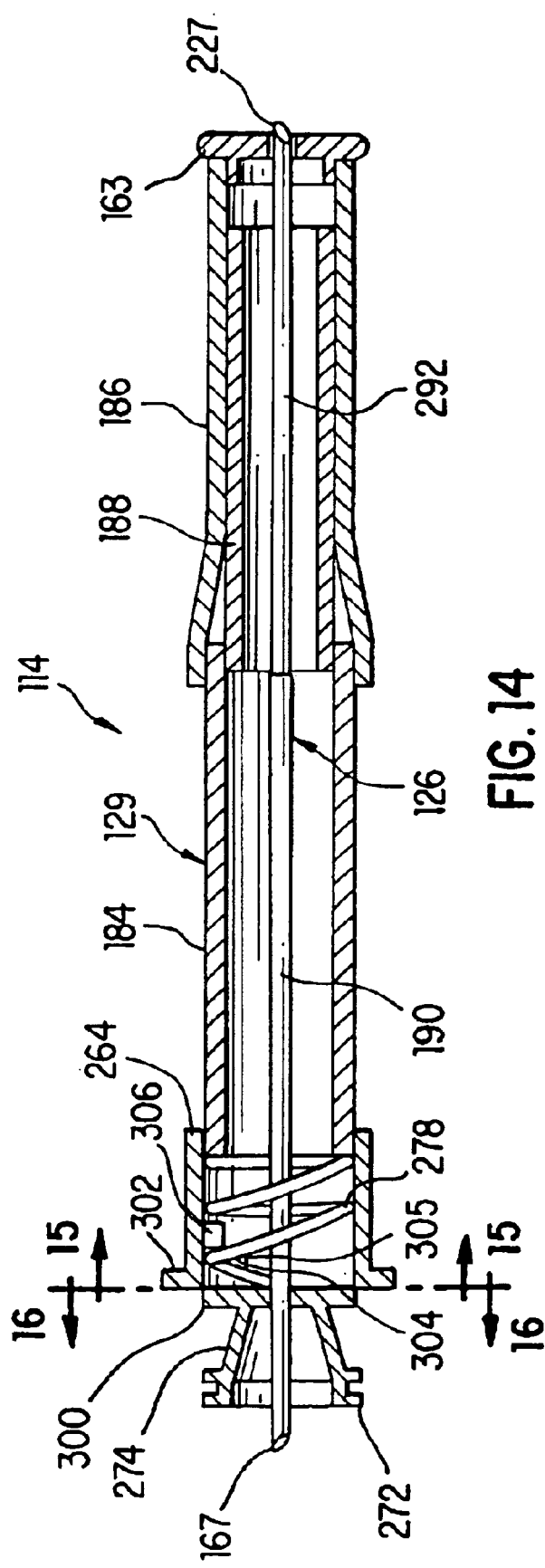
FIG. 14 is a longitudinal cross sectional view of an alternate embodiment of the catheter in accordance with the present invention.

FIG. 14 is a longitudinal cross sectional view of catheter 114 including an alternate manifold 264 and alternate distal tube 292. Alternate distal tube 292 is preferably formed from Nitinol hypotube. Tube 292 preferably has a distal tip 227 in the form of a lancet tip which reduces coring of myocardial tissue during use. Each of the tips disclosed in the embodiments described above could also be lancet tips. The tips are preferably 30 to 23 gage, although larger or smaller diameter tips can be used.

Manifold 264 includes a flange 302 which could be used to engage a portion of gun body 116 in a manner similar to that of flange 168 of manifold 164 described above. Within manifold 262 includes a plurality of steps 304, 305 and 306 disposed therein. Disposed proximate the proximal end of proximal portion 190 of inner shaft 126 is an alternate embodiment of a Luer fitting 274, which can engage Luer fitting 128 of syringe 118 of gun 116. Luer fitting 274 includes threads 272. At the distal end of Luer fitting 274 is a step engaging member 300. A spring 278 is fixed at its proximal end within manifold 274 and at its distal end to Luer fitting 274. Spring 278 is biased to draw Luer fitting 274 distally.

Figure 15:
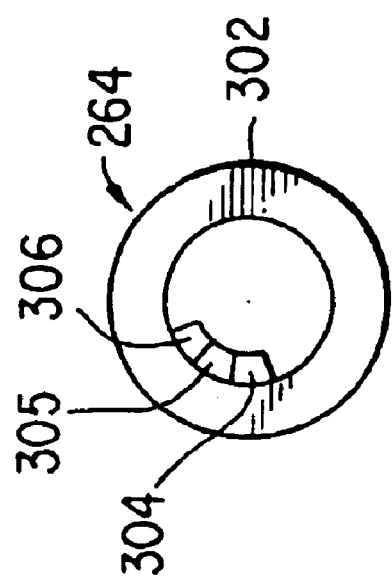
FIG. 15 is a proximal end view of an embodiment of a manifold in accordance with the present invention.

FIG. 15 is a view of the proximal end of manifold 264 taken from FIG. 14. Steps 304, 305 and 306 can be seen within manifold 264. It can be appreciated by reference made to FIG. 14 that each of the steps is disposed successively more distally than the preceding step.

Figure 16:
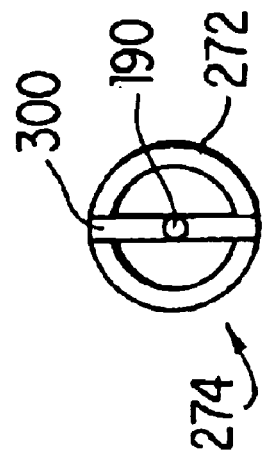
FIG. 16 is a distal end view of an embodiment of a Luer fitting in accordance with the present invention.

FIG. 16 is, a view of the distal end of Luer fitting 274 taken from FIG. 14. Elongate step engaging member 300 can be seen. It can be appreciated that if step engaging member 300 has a length approximately equal to, but less than the inside diameter of manifold 264, it can slide within manifold 264 to engage against steps 304, 305 or 306 depending upon the angular position of step engaging member 300 about the longitudinal axis of catheter 114. The more distally disposed the step within manifold 264, the more distally step engaging member 300 can move within manifold 264 prior to engaging a given step.

It can be appreciated that the further engaging member 300 advances distally, the farther inner shaft 126 and thus distal tip 227 will advance distally. Thus, using manifold 264 and Luer fitting 274, the depth of penetration into the heart wall of tip 227 can be controlled. It is, in fact, contemplated that the depth of penetration could be adjusted such that tip 222 would completely penetrate the heart wall to dispose tip 227 between the epicardium and the pericardial. sac. If tip 227 is disposed in such a location, catheter 114 could be used to deliver drugs, growth factors or other therapeutic agents or fluids within the pericardial sac.

It can be appreciated that the distal. movement of inner shaft 126 can be limited by steps 304, 305 or 306 or manifold 264, by configuration as shown with respect to manifold 164 above, or by swage 196 engaging hood 163 as shown in FIG. 10. By relying on a stop disposed at the distal end of catheter 114, the depth of penetration of inner shaft tip 127 into the myocardium can be more consistently controlled. This is facilitated by making the length of inner shaft 126 sufficiently long that regardless of the bending of catheter 114 along the atrial access path, swage 196 will engage hood 163 when shaft 126 is advanced distally. It can also be appreciated that a variable depth control device such as that described with connection to manifold 264 could be disposed at the distal end of catheter 114.

Figure 17:
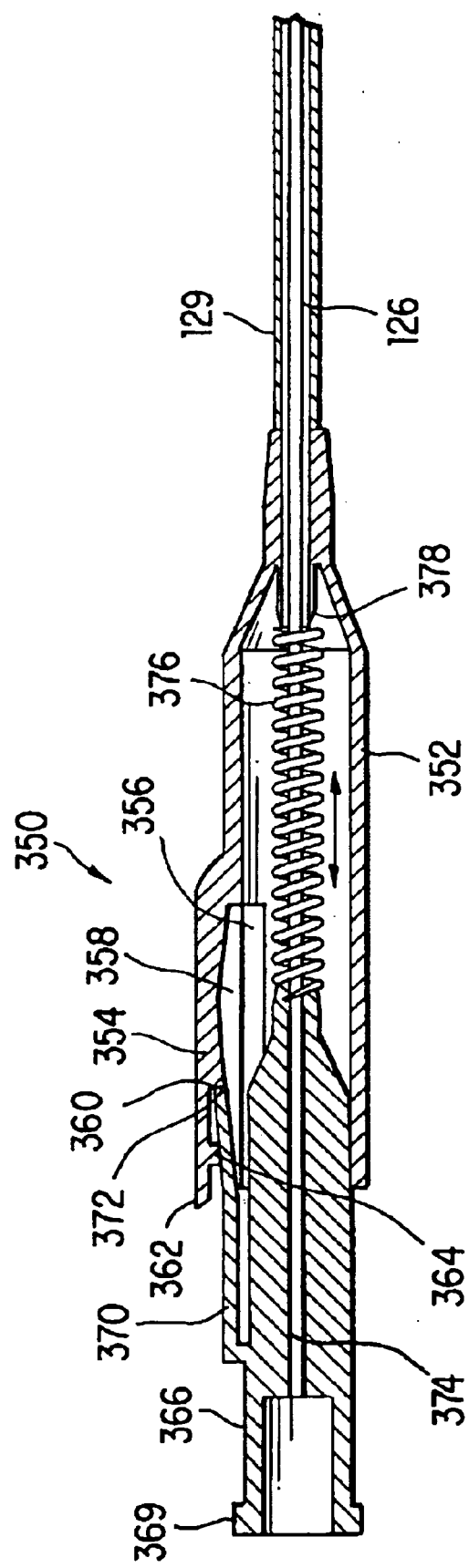
FIG. 17 is a cross sectional view of an alternate manifold in accordance with the present invention.

FIG. 17 is a cross sectional view of an alternate embodiment of a manifold 350 in accordance with the present invention. Manifold 350 can be disposed at the proximal end of outer shaft 129. Inner shaft 126 can extend through outer shaft 129 into manifold 350. Manifold 350 preferably includes a housing 352 having on one side a lever arm 354 extending therefrom, in a proximal direction. Lever arm 354 is preferably disposed adjacent an elongate, longitudinally extending groove 356 defined in housing 352. Lever arm 354 preferably extends over an area 358 between lever arm 354 and groove 356. Lever arm 354 preferably includes a restraining notch 360 disposed distally of its proximal end 362. A strut 364 extends from lever arm 354 proximate distal end 362. Housing 356 is preferably formed from a polymer or other materials as known to those skilled in the art. The material from which lever arm 354 is formed is preferably elastic enough that it can be bent or pressed inwardly toward groove 356.

Slidably disposed within housing 352 is a fitting 366 which can be a Luer fitting having threads 368. Fitting 366 is slidable proximally and distally in the direction shown by the arrows. Fitting 366 is preferably connected at its distal end to inner shaft 126 and preferably defines a lumen 174 extending therethrough in fluid communication with the lumen through inner shaft 126. The catch arm 370 extends in a distal direction to its distal end 372. Fitting 366 is preferably formed from a polymer or other material known to those skilled in the art. The material from which catch arm 370 is formed is preferably elastic enough that arm 370 can be pressed inwardly toward groove 356.

A helical spring coil 376 is preferably disposed around a portion of inner shaft 126. Spring 376 has a proximal end and a distal end. The proximal end of spring 376 is connected to the distal end of fitting 366 and the distal end of spring 376 is connected to an anchor 378 extending from housing 352. As shown in FIG. 17, spring 376 has been elongated by pulling fitting 366 proximally such that distal end 372 of catch arm 370 engages notch 360 of lever arm 354 and strut 364 of arm 354 rests against a portion of catch 370. In this configuration, fitting 366 is in a first position disposed proximally within housing 352 such that distal end 127 of inner shaft 126 is disposed within outer shaft 129. Fitting 366 can be released from the first position and moved proximally by depressing proximal end 362 of lever arm 354 toward catch 370. The distal end of catch arm 372 will then disengage from notch 360 such that catch arm 370 moves into space 358 as fitting 366 moves distally to a second position as spring 376 recoils. In the second position, distal end 127 of inner shaft 126 extends beyond hood 163 of outer shaft 129 (as shown in FIG. 10). The amount of travel distally into the second position is limited by engagement of swage 196 with hood 163.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method for delivering a therapeutic implant to a tissue comprising:
   providing an elongate catheter having a distal end including a lumen;
   providing a carrier including a therapeutic agent;
   placing the carrier including the therapeutic agent into the lumen;
   advancing the distal end of the catheter to the tissue;
   depositing the carrier including the therapeutic agent into the tissue;
   withdrawing the catheter; and
   leaving the carrier and therapeutic agent in the tissue after the catheter has been withdrawn.

2. The method in accordance with claim 1, wherein the tissue to be treated is ischemic heart tissue.

3. The method in accordance with claim 2, wherein the therapeutic agent is selected from the group consisting of VEGF, FGF, PDGF, estrogen, HIF1-α, Akt, DEL-1, angiopoietins and combinations thereof.

4. The method in accordance with claim 2, wherein the therapeutic agent includes genes effecting the production of growth factors.

5. The method in accordance with claim 2, wherein the therapeutic agent includes genetically engineered cells.

6. The method in accordance with claim 2, wherein the therapeutic agent includes healthy tissue.

7. The method in accordance with claim 2, wherein the therapeutic agent includes cells.

8. The method in accordance with claim 1, wherein the tissue includes failing heart tissue.

9. The method in accordance with claim 8, wherein the therapeutic agents are selected from the group consisting of positive inotripic, diuretics vasodilators, neurohormonal antagonists, calcium channel blockers, anti-ischemic agents, anti-arrhythmics, anticoagulants, natiruretic peptides, growth hormones, and adenosine receptor antagonists and combination thereof.

10. The method in accordance with claim 1, wherein the tissue includes heart tissue following myocardial infarction.

11. The method in accordance with claim 10, wherein the therapeutic agents are selected from the agents consisting of AKT kinases, adenylyl cylase VI, angiogenisis inducing agents and combinations thereof.

12. The method in accordance with claim 1, wherein the tissue to be treated includes cancerous tissue.

13. The method in accordance with claim 12, wherein the therapeutic agents are selected from the group consisting of cytoxic proteins, cytostatic agents, genes, anti-angiogenic molecules and combinations thereof.

14. The method of claim 1 wherein the catheter includes a first lumen and a second lumen, the first lumen having a sharpened distal tip and the second lumen having a sharpened distal tip.

15. The method of claim 1 wherein the carrier is a polymer.

16. The method of claim 14 wherein the second lumen includes a cross-linking agent for ejection from the second lumen.

* * * * *

UNITED STATES PATENT AND TRADEMARK OFFICE
CERTIFICATE OF CORRECTION

PATENT NO. : 6,953,466 B2
DATED : October 11, 2005
INVENTOR(S) : Palasis et al.

It is certified that error appears in the above-identified patent and that said Letters Patent is hereby corrected as shown below:

Column 17,
Line 3, change "inventions's" to -- invention's --;

Column 18,
Line 5, change "positive inotripic, diuretics vasodilators," to -- positive inotropics, diuretics, vasodilators, --;
Line 8, change "natiruretic" to -- natriuretic --;
Line 15, change "angiogenisis inducing" to -- angiogenesis-inducing --.

Signed and Sealed this

Seventh Day of March, 2006

JON W. DUDAS
*Director of the United States Patent and Trademark Office*